US008848938B2

(12) United States Patent
Opfer

(10) Patent No.: US 8,848,938 B2
(45) Date of Patent: Sep. 30, 2014

(54) ELECTROSTATIC PLANAR LOUDSPEAKER ARRANGEMENT IN A MOTOR VEHICLE

(75) Inventor: Holger Opfer, Hannover (DE)

(73) Assignee: Volkswagen AG, Wolfsburg (DE)

(*) Notice: Subject to any disclaimer, the term of this patent is extended or adjusted under 35 U.S.C. 154(b) by 1277 days.

(21) Appl. No.: 11/664,767

(22) PCT Filed: Sep. 28, 2005

(86) PCT No.: PCT/EP2005/010631

§ 371 (c)(1),
(2), (4) Date: Aug. 30, 2007

(87) PCT Pub. No.: WO2006/037586

PCT Pub. Date: Apr. 13, 2006

(65) Prior Publication Data

US 2008/0192953 A1 Aug. 14, 2008

(30) Foreign Application Priority Data

Oct. 4, 2004 (DE) ......................... 10 2004 048 990

(51) Int. Cl.

| | |
|---|---|
| ***A61F 11/06*** | (2006.01) |
| ***G10K 11/16*** | (2006.01) |
| ***H03B 29/00*** | (2006.01) |
| ***H04R 5/02*** | (2006.01) |

(52) U.S. Cl.

CPC .............. *H04R 5/02* (2013.01); *H04R 2499/13* (2013.01); *H04R 2440/01* (2013.01)

USPC .......................................... 381/71.2; 381/71.4

(58) Field of Classification Search

USPC ............ 381/86, 302, 71.4, 99, 389, 152, 386, 381/190, 71.2; 379/417

See application file for complete search history.

(56) References Cited

U.S. PATENT DOCUMENTS

| | | | | |
|---|---|---|---|---|
| 1,782,278 | A * | 11/1930 | Vogt | 381/174 |
| 2,631,196 | A * | 3/1953 | Janszen | 381/116 |
| 3,008,013 | A * | 11/1961 | Peter et al. | 381/182 |
| 3,773,984 | A * | 11/1973 | Walker | 381/96 |
| 3,931,469 | A * | 1/1976 | Elliott et al. | 381/99 |
| 5,754,664 | A * | 5/1998 | Clark et al. | 381/86 |
| 5,949,892 | A * | 9/1999 | Stewart | 381/113 |
| 6,198,831 | B1 * | 3/2001 | Azima et al. | 381/338 |
| 6,343,129 | B1 * | 1/2002 | Pelrine et al. | 381/191 |
| 6,411,723 | B1 * | 6/2002 | Lock et al. | 381/431 |

(Continued)

FOREIGN PATENT DOCUMENTS

| | | |
|---|---|---|
| CN | 2 325 948 | 6/1999 |
| CN | 1 310 575 | 8/2001 |

(Continued)

OTHER PUBLICATIONS

International Preliminary Report on Patentability and Written Opinion, PCT International Patent Application No. PCT/EP2005/010631, dated Apr. 24, 2007 (English-language translation).

(Continued)

*Primary Examiner* — Alexander Jamal

(74) *Attorney, Agent, or Firm* — Kenyon & Kenyon LLP

(57) ABSTRACT

A loudspeaker arrangement in a motor vehicle includes at least one loudspeaker, which is able to be driven by an audio processor, the loudspeaker being arranged as at least one electrostatic planar loudspeaker.

11 Claims, 2 Drawing Sheets

(56) References Cited

U.S. PATENT DOCUMENTS

| | | | | |
|---|---|---|---|---|
| 6,580,374 | B2 * | 6/2003 | Schrage | 340/933 |
| 6,842,964 | B1 * | 1/2005 | Tucker et al. | 29/594 |
| 6,968,065 | B1 * | 11/2005 | Gu | 381/111 |
| 6,980,663 | B1 * | 12/2005 | Linhard | 381/86 |
| 7,062,064 | B2 * | 6/2006 | Bachmann et al. | 381/431 |
| 7,415,116 | B1 | 8/2008 | Fels | |
| 2002/0122561 | A1 | 9/2002 | Pelrine et al. | |
| 2005/0259831 | A1 * | 11/2005 | Hutt et al. | 381/86 |
| 2008/0192953 | A1 * | 8/2008 | Opfer | 381/86 |

FOREIGN PATENT DOCUMENTS

| | | |
|---|---|---|
| DE | 199 58 836 | 5/2001 |
| DE | 100 40 994 | 3/2002 |
| JP | 2004-056564 | 2/2004 |
| WO | 97/16048 | 5/1997 |
| WO | 99/56498 | 11/1999 |
| WO | 01/15489 | 3/2001 |

OTHER PUBLICATIONS

Morton, "Meres first to get revolutionary speakers", Automotive Engineer, professional engineering publishing, London, GB, Bd. 25, Nr. 10, Nov. 2000.

* cited by examiner

ELECTROSTATIC PLANAR LOUDSPEAKER ARRANGEMENT IN A MOTOR VEHICLE

FIELD OF THE INVENTION

The present invention relates to a loudspeaker arrangement in a motor vehicle.

BACKGROUND INFORMATION

Loudspeaker arrangements in a motor vehicle are used primarily for emitting audio signals. The audio signal sources are, for instance, radios, CD players, MP3 players or DVD players. In addition to that, the loudspeakers are used for emitting acoustical data, of a navigation system, for instance, and/or a parking aid assistance system.

Customary loudspeakers in a motor vehicle are constructed as electrodynamic loudspeakers having permanent magnets. These are relatively voluminous and heavy, and, because of the limited available space in a motor vehicle, this often leads to compromises between installation location and emission characteristic.

A planar loudspeaker is described in Japanese Published Patent Application No. 2004-56564, which is situated behind the roofliner, so that there is a greater degree of freedom with regard to size and shape.

A method is described in German Published Patent Application No. 199 58 836 for improving communications in a vehicle, the voice signals of the passengers of a vehicle being recorded individually for each passenger via a microphone assigned to him within the scope of his seat. The recorded voice signals are amplified separately for each passenger in an input step and are filtered for start level minimization and frequency adjustment. The amplified and filtered voice signals of each individual passenger are submitted to a signal processing that is individual for each output channel, in the form of a propagation delay correction and a level differentiation, for the partition to the output channels and therewith for the partition to the individual components for a voice output device made up of loudspeakers, as a function of the local assignment of the microphone in the vehicle, via which the voice signal was recorded and as a function of the local assignment of each individual loudspeaker of the voice output device in the vehicle, via which the voice signal is to be output, via a summation step and a distribution step. The assignment of the voice signals that were individually processed for each output channel to the individual output channels and thus to the individual loudspeakers of the voice output device takes place via an adjustment stage in which, via a level adjustment and a frequency adjustment, there takes place an adjustment, tuned to each output channel and therewith to each loudspeaker of the voice output device, of the respective voice signal to the spatial conditions of the vehicle and the desired volume. The microphone may be arranged as a directional microphone, in this context. Furthermore, a use as a telephone device having a free assignment of users within the vehicle is suggested. In the case of a use within the framework of telephone processes, the structure of the device makes it possible for a conversation to be assigned, for example, to each seat and, thus, to each occupant. In this context, the reproduction may take place as a controlled process via selected loudspeakers, so that even selected vehicle occupants may participate in the phone conversation. At the same time, it is possible to limit the extent to which other occupants in specific seats overhear the conversation. This is done by switching the incoming signal to loudspeakers chosen for this and by processing it as a fictive, i.e., virtual voice source. The outgoing signal(s) undergo(es) the same process as the signal which is utilized for the internal communication. It is possible to adjust the manner in which specific seats or areas are separated both from the receiving, as well as from the reproduction side, using operating units of the control unit.

An acoustical element is described in PCT International Published Patent Application No. WO 99/56498, that includes at least two porous layers which are electrically conductive or are metallized on one side. Between the two porous layers there is situated an insulated plastic layer which is preferably arranged in two layers, there being a metallic coating between the two layers via which the plastic layer can be loaded to a certain electrical potential. The plastic layer is connected to the porous layers at certain places. Between two such boundary positions there is an air gap between the porous layers and the plastic layer. By applying a signal to at least one porous layer, the plastic layer is then set into vibration, the other porous layer preferably also having the signal, that is in phase opposition, applied to it. This arrangement represents an electrostatic planar loudspeaker.

SUMMARY

Example embodiments of the present invention may provide a loudspeaker arrangement in a motor vehicle that is better adapted to the structural conditions in a motor vehicle.

To do this, the at least one loudspeaker is arranged as an electrostatic planar loudspeaker. This may provide, compared to the usual electrodynamic loudspeakers, that it is extremely flat, and, because of this and based on the materials used, it is easily flexible, which simplifies integrating it into motor vehicle structural parts. A further aspect is that the planar loudspeaker, which is not actively driven, acts automatically as a damper for high frequencies of greater than 1 kHz, for instance, and it thus dampens interfering noises.

The loudspeaker arrangement may include at least two adjacent planar loudspeakers, which are able to be driven using different complex transfer functions for adjusting an emission characteristic. The emission characteristic can be considerably improved thereby, especially at low frequencies, since otherwise, at low frequencies, minor lobes come about, which lead to crosstalk to adjacent vehicle seats. On the other hand, using the complex transfer functions, a directional loudspeaker can be set over the entire audio frequency. This is considered to be of advantage especially if specifically only data for a person are to be emitted, for instance, acoustical driving direction instructions of a navigation system. In this context, the complex transfer functions can be fixedly set or can be changed adaptively, in order to set an emission characteristic with regard to opening angle and/or direction, adapted to the respective conditions. A directional speaker may include an acoustical source which emits differently in different spatial directions, the alignment with the strongest emission (main lobe) being designated by an angle of 0°. The quality of a directional emitter or directional speaker is generally determined by a planar extension of the emitter compared to the wavelength of the frequency in question. One possible aspect of the directional speaker is that, for frequencies whose wavelength is less than the extension of the emitter at right angles to the alignment of the emitter, all minor lobes of the directional characteristic deviating above 45° from the alignment of the emitter are less by at least −10 dB.

The various planar loudspeakers may be arranged concentrically about one another, so that an emission characteristic can be set that is symmetrical about the emission direction, which may have a very low opening angle. For this, the planar loudspeakers are arranged either as rings or as rectangles or squares that are arranged around one another.

Alternatively, the planar loudspeakers can be positioned next to one another in the form of strips, so that at least transverse crosstalk is avoided. An aspect of this arrangement is a simple design.

At least two adjacently placed planar loudspeakers can optionally be operated as a stereo loudspeaker or as a directional loudspeaker. The user is able to select, in this context, whether this might prefer to have a stereo sound, for example, in the case of music reproduction, or a good directional characteristic, in order not to disturb the other passengers.

The loudspeaker arrangement may include at least one second loudspeaker, any crosstalk being able to be ascertainable and/or recordable, the second loudspeaker being able to be driven using a signal that is in phase opposition to the crosstalk. This corresponds to the principle of active noise cancellation (ANC), which is extremely well known in theory and practice. In this instance, the first loudspeaker is assigned, for example, to the driver, and the second loudspeaker is assigned, for example, to the front passenger, the first and/or second loudspeaker being able to be formed in each case by a plurality of planar loudspeakers, so that particularly the improvement of the emission characteristic can be combined with the ANC.

The crosstalk can be determined or estimated ahead of time. If the emission characteristic and the transfer function are known, the crosstalk to the second loudspeaker can be calculated from the signal of the first loudspeaker that is sent. The crosstalk may be recorded. To do this, at least one microphone is used. In addition, another advantageous property of electrostatic loudspeakers can be taken advantage of, namely, that they can be relatively simply operated also as microphones. If no signal voltage is actively applied to the porous layers, a soundwave leads to an excursion of the plastic layer, which results in a voltage change at the electrodes of the porous layers, which can be picked off as a signal voltage. Therefore, it is possible, by turns, to use the loudspeakers also as microphones.

The planar loudspeakers may be integrated into the roofliner, since at that place there is relatively much installation space for the flat loudspeakers.

The directional microphones and/or the directional speakers may be integrated into the roofliner using a quick-change frame, the two panel sides of a directional speaker and/or a directional microphones, possibly having different themes. This makes use of the aspect that the electrostatic panels are arranged symmetrically. Using the different themes, one theme may, for instance be adapted to the roofliner, whereas the other may have a children's decor.

The roofliner itself may be formed from the panel material of the planar loudspeaker. Areas of panels can then be specified as loudspeakers, microphones or supply leads by appropriate patterning. The roofliner hereby becomes a multifunctional element. The porous layer is arranged as an insulator, which is metallized on the side facing the plastic layer. Because of this, there is no voltage present on the side of the roofliner facing the passenger cell.

At least one bending wave loudspeaker may be integrated into the roofliner, which can be switched on or off as required. When playing music, for example, the user can hereby select the bending wave loudspeaker, whereas, during support of a verbal communication, he can utilize the directional characteristic of the planar loudspeaker.

A frequency dividing network is assigned to the planar loudspeakers, the frequency components of, e.g., less than 250 Hz, e.g., less than 200 Hz, being output in phase to all planar loudspeakers. In addition, the frequency divider may be able to be switched on or off. When the frequency dividing network is switched on, the sound pressure for low frequencies can then be increased, which may be desirable for music reproduction. When the frequency dividing network is switched off, on the other hand, as described before, the directional characteristic of the loudspeakers can be set, for instance, by the selection of different complex transfer functions.

Example embodiments of the present invention are described in more detail below with reference to the appended Figures.

DETAILED DESCRIPTION

Figure 1:
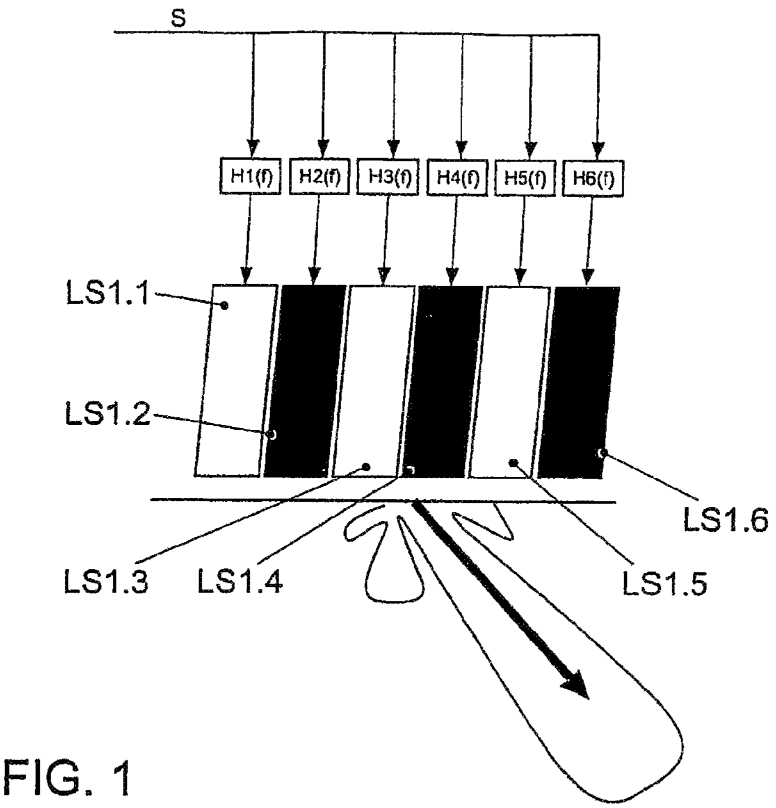
FIG. 1 is a schematic view of a plurality of planar loudspeakers, arranged in the form of strips.

FIG. 1 schematically shows a loudspeaker arrangement 1 in a motor vehicle. Loudspeaker arrangement 1 includes a plurality of strip-shaped electrostatic planar loudspeakers LS 1.1 to LS 1.6, situated next to one another, which are assigned to a region of the motor vehicle, for instance, to the driver'seat. Each of the planar loudspeakers LS 1.1 to LS 1.6 has a preconnected filter function H1(f)-H6(f), and each has the same signal s applied to it. By a suitable selection of the complex filter functions H1(f)-H6(f) a beam forming can be achieved, using which one is able to suppress minor lobes in one direction. In the example shown, the right minor lobe to the front passenger seat is suppressed. By changing the complex filter functions H1(f)-H6(f), the main lobe may be swiveled, so that an alignable directional loudspeaker can be implemented.

Figure 2:
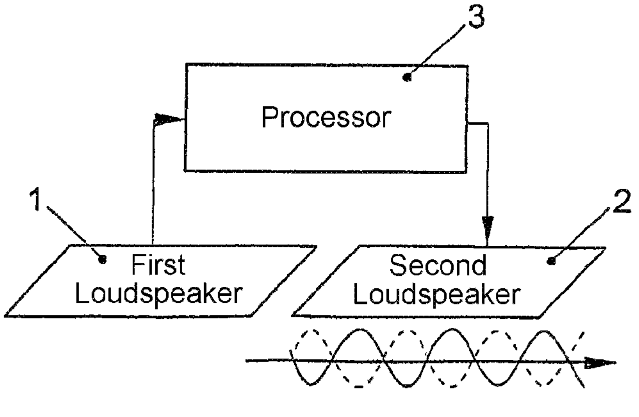
FIG. 2 is a schematic view of two planar loudspeakers for an ANC.

In FIG. 2 it is shown schematically how crosstalk can be reduced additionally or alternatively. The arrangement includes one first planar loudspeaker 1, which is, for example, assigned to the driver's seat, and a second planar loudspeaker 2, which is, for example, assigned to the front passenger seat. It is assumed, in this instance, that planar loudspeaker 1 emits a signal that leads to crosstalk at the front passenger seat. This crosstalk is symbolized by the sinusoidal solid line wave. A processor 3 calculates, with the aid of a known transfer function HFB from the driver's seat to the front passenger seat and the emitted signal, how the crosstalk looks, and drives the second planar loudspeaker using the crosstalk signal that is in phase opposition (shown by a dashed line), so that a cancellation comes about in the ideal case.

Figure 3:
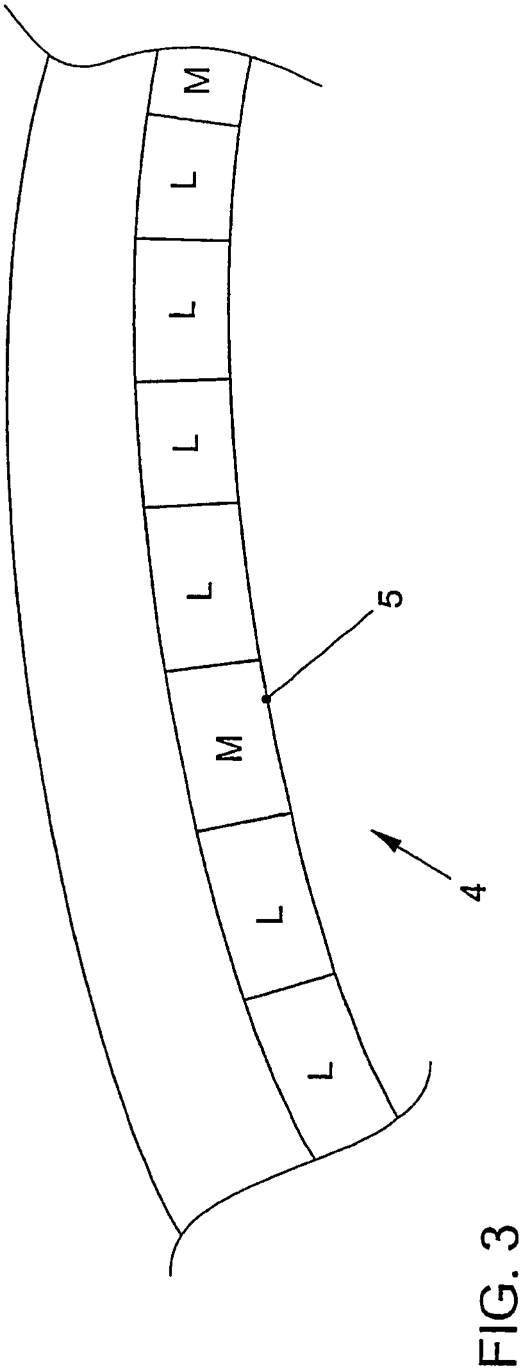
FIG. 3 is a schematic view of an integration into the roofliner.

FIG. 3 shows schematically how electrostatic loudspeakers L and microphones M are integrated in a roofliner 4. Roofliner 4 itself is made up of a panel material, the outer surface 5 of the one porous layer forming the visible part of roofliner 4. Using a template or similar lithographic process, the electrical supply leads are specified, so that areas are defined that operate as a loudspeaker or as a microphone. It should be mentioned, in this connection, that, when motor vehicles are mentioned, this also includes airplanes, trains, etc., besides automobiles of all types and sizes.

What is claimed:

1. A loudspeaker arrangement in a motor vehicle, comprising:
   - at least one first electrostatic planar loudspeaker drivable by an audio processor;
   - wherein at least one second loudspeaker is arranged in the motor vehicle, crosstalk from the first loudspeaker to the second loudspeaker drivable by a signal in phase opposition to the crosstalk;
   - wherein the at least one second loudspeaker is arranged as an electrostatic planar loudspeaker; and
   - wherein the at least one second planar loudspeaker is configured to be switched over to operate as a microphone to record the crosstalk from the at least one first loudspeaker.

2. The loudspeaker arrangement according to claim 1, wherein the loudspeaker arrangement includes at least two adjacent planar loudspeakers drivable by different complex transfer functions to set an emission characteristic.

3. The loudspeaker arrangement according to claim 1, wherein the loudspeakers are integrated into a roofliner of the motor vehicle.

4. The loudspeaker arrangement according to claim 3, wherein the roofliner is formed from panel material of the planar loudspeaker.

5. The loudspeaker arrangement according to claim 4, wherein the panel material is patterned to define areas of the panel material as at least one of (a) loudspeakers, (b) microphones and (c) supply leads.

6. The loudspeaker arrangement according to claim 1, wherein at least one bending wave loudspeaker is integrated into a roofliner of the motor vehicle.

7. The loudspeaker arrangement according to claim 1, further comprising a frequency dividing network assigned to the planar loudspeakers, frequency components of less than 250 Hz being output in phase to all planar loudspeakers.

8. A loudspeaker arrangement in a motor vehicle, comprising:
   - at least one first electrostatic planar loudspeaker; and
   - an audio processor configured to drive the first loudspeaker;
   - wherein at least one second loudspeaker is arranged in the motor vehicle, crosstalk from the first loudspeaker to the second loudspeaker drivable by a signal in phase opposition to the crosstalk;
   - wherein the at least one second loudspeaker is arranged as an electrostatic planar loudspeaker; and
   - wherein the at least one second planar loudspeaker is configured to be switched over to operate as a microphone to record the crosstalk from the at least one first loudspeaker.

9. A motor vehicle, comprising:
   - a loudspeaker arrangement in a motor vehicle including:
     - at least one first electrostatic planar loudspeaker; and
     - an audio processor configured to drive the first loudspeaker;
     - wherein at least one second loudspeaker is arranged in the motor vehicle, crosstalk from the first loudspeaker to the second loudspeaker drivable by a signal in phase opposition to the crosstalk;
     - wherein the at least one second loudspeaker is arranged as an electrostatic planar loudspeaker; and
     - wherein the at least one second planar loudspeaker is configured to be switched over to operate as a microphone to record the crosstalk from the at least one first loudspeaker.

10. The loudspeaker arrangement according to claim 2, wherein the planar loudspeakers are arranged concentrically to one another.

11. The loudspeaker arrangement according to claim 2, wherein the planar loudspeakers are arranged next to one another in the form of strips.

* * * * *